(12) United States Patent
Kim et al.

(10) Patent No.: US 12,173,210 B2
(45) Date of Patent: Dec. 24, 2024

(54) SOLVENTLESS QUANTUM DOT COMPOSITION, METHOD FOR PRODUCING SAME, AND CURED FILM, COLOR FILTER, AND DISPLAY DEVICE COMPRISING SAME

(71) Applicants: HANSOL CHEMICAL CO.,LTD, Seoul (KR); SAMSUNG DISPLAY CO., LTD., Gyeonggi-do (KR)

(72) Inventors: Gilran Kim, Jeollabuk-do (KR); Yunju Bae, Jeollabuk-do (KR); Ahyoung Jo, Jeollabuk-do (KR); Shulgi Park, Jeollabuk-do (KR); Eunhee Nam, Jeollabuk-do (KR); Sungmin Ha, Jeollabuk-do (KR); Chunrae Nam, Jeollabuk-do (KR); Sunyoung Kwon, Gyeonggi-do (KR); Buyong Kim, Gyeonggi-do (KR); Jinwon Kim, Gyeonggi-do (KR); Hye-Jin Paek, Gyeonggi-do (KR); Taeyoung Song, Gyeonggi-do (KR)

(73) Assignees: HANSOL CHEMICAL CO.,LTD, Seoul (KR); SAMSUNG DISPLAY CO., LTD., Gyeonggi-do (KR)

( * ) Notice: Subject to any disclaimer, the term of this patent is extended or adjusted under 35 U.S.C. 154(b) by 0 days.

(21) Appl. No.: 18/692,656

(22) PCT Filed: Sep. 19, 2022

(86) PCT No.: PCT/KR2022/013950
§ 371 (c)(1),
(2) Date: Mar. 15, 2024

(87) PCT Pub. No.: WO2023/054952
PCT Pub. Date: Apr. 6, 2023

(65) Prior Publication Data
US 2024/0287382 A1  Aug. 29, 2024

(30) Foreign Application Priority Data

Sep. 28, 2021 (KR) .................. 10-2021-0128262

(51) Int. Cl.
| | | |
|---|---|---|
| *C09K 11/02* | (2006.01) |
| *C09D 11/037* | (2014.01) |
| *C09D 11/101* | (2014.01) |
| *C09D 11/107* | (2014.01) |
| *C09D 11/322* | (2014.01) |
| *C09D 11/50* | (2014.01) |
| *C09K 11/08* | (2006.01) |
| *C09K 11/88* | (2006.01) |
| *G02B 5/20* | (2006.01) |
| *B82Y 20/00* | (2011.01) |
| *B82Y 40/00* | (2011.01) |

(52) U.S. Cl.
CPC .......... *C09K 11/025* (2013.01); *C09D 11/037* (2013.01); *C09D 11/101* (2013.01); *C09D 11/107* (2013.01); *C09D 11/322* (2013.01); *C09D 11/50* (2013.01); *C09K 11/0883* (2013.01); *C09K 11/883* (2013.01); *G02B 5/20* (2013.01); *B82Y 20/00* (2013.01); *B82Y 40/00* (2013.01)

(58) Field of Classification Search
CPC ....... C09K 11/025; C09K 11/02; C09K 11/08; C09K 11/0811; C09K 11/0883; C09K 11/54; C09K 11/565; C09K 11/883; C09D 11/101; C09D 11/107; C09D 11/322; C09D 11/50; G02B 5/20; B82Y 20/00; B82Y 40/00
See application file for complete search history.

(56) References Cited

U.S. PATENT DOCUMENTS

2021/0226172 A1* 7/2021 Chung .................. C09K 11/06

FOREIGN PATENT DOCUMENTS

| CN | 111518543 A | 8/2020 |
| KR | 10-1350257 B1 | 1/2014 |
| KR | 10-2019-0050726 A | 5/2019 |
| KR | 10-2020-0090493 A | 7/2020 |
| KR | 10-2021-0109112 A | 9/2021 |
| WO | 2022163950 A1 | 8/2022 |

OTHER PUBLICATIONS

WIPO/ISA/KR, International Search Report and Written Opinion issued in corresponding International Application No. PCT/KR2022/013950 on Dec. 27, 2022, 7 pages.

* cited by examiner

*Primary Examiner* — Matthew E. Hoban
*Assistant Examiner* — Lynne Edmondson
(74) *Attorney, Agent, or Firm* — J. Peter Paredes; Amin Wasserman Gurnani LLP

(57) ABSTRACT

A solventlesss quantum dot composition, a method for preparing the same, and a cured film, a color filter, and a display device including the same are disclosed. The solventless quantum dot composition comprises quantum dots surface-modified with at least two ligands, has low viscosity and good optical properties, and can be prepared by synthesis of quantum dots (QDs), followed by direct ligand substitution in the solution, thereby securing a simplified preparation process.

20 Claims, No Drawings

SOLVENTLESS QUANTUM DOT COMPOSITION, METHOD FOR PRODUCING SAME, AND CURED FILM, COLOR FILTER, AND DISPLAY DEVICE COMPRISING SAME

CROSS-REFERENCE TO RELATED APPLICATIONS

The present application claims priority to PCT application serial no. PCT/KR2022/013950 filed Sep. 19, 2022, which claims priority to Korean patent application serial no. 10-2021-0128262, Sep. 28, 2021, each herein incorporated by reference in their entireties.

TECHNICAL FIELD

The present invention relates to a solventless quantum dot composition, a method for preparing the same, and a cured film, a color filter and a display device including the same. Specifically, the solventless quantum dot composition according to the present invention includes quantum dots subjected to surface modification with two or more ligands, has low viscosity and good optical properties, and can be prepared by ligand substitution directly in a corresponding solution after preparation of quantum dots (QDs), thereby simplifying a preparation process.

BACKGROUND ART

In general, quantum dots (QDs), also known as semiconductor nanocrystals, are attracting attention as next generation light emitting elements, since the quantum dots can emit various colors through generation of light with different wavelengths depending on particle size without changing the kind of substance and have advantages of better color purity and photo-stability than typical light emitting materials.

In particular, as new trend in the field of displays, quantum dots can be applied to various displays, electronic devices and the like other than TVs and LEDs. Quantum dots represented by CdSe, InP, and the like have achieved rapid improvement in luminous efficacy (quantum yield) and various methods for synthesis of quantum dots with luminous efficacy close to 100% have been introduced in the art. As a result, TVs with quantum dot sheets are commercialized in the art. As a next step, quantum dot TVs that are self-emissive, as opposed to quantum-dot LED TVs in which light is filtered through color-filter layers incorporating quantum dots (excluding pigments and dyes), are being developed. In development of such quantum dot TVs, a main issue is how long the quantum dots can maintain optical efficiency in a process of constituting pixels and a manufacturing process.

On the other hand, materials for color filters require high sensitivity, adhesion to substrates, chemical resistance, heat resistance, and the like. Color filters applied to typical displays are generally produced through a patterning process in which a desired pattern is formed by exposure through a photomask formed of a photosensitive resist composition, followed by development to dissolve and remove non-exposed portions of the photomask.

Recently, in order to respond to advances of materials used in pixels and to address increase in manufacturing costs caused thereby, there has been a growing interest in methods that reduce use of a material as much as possible by applying the material only to a desired region instead of patterning through spin coating or slit coating as in the art. The most representative method is an inkjet method, in which materials are used only for desired pixels to prevent waste of the materials.

However, since a quantum dot composition used in the inkjet method is required to have a viscosity of 100 cP or less, preferably 50 cP or less, the composition contains a solvent to realize low viscosity. The presence of the solvent in the quantum dot composition causes a severe deviation in thickness after curing, a limitation in increase in film thickness, and concerns about environmental pollution due to use of organic solvents.

Accordingly, the applicant of the present invention, Han-Sol Chemical Co., Ltd., has applied for a solventless quantum dot composition, a preparation method thereof, and a cured film, color filter and display device comprising the same (No. 10-2021-0011711). This application relates to a quantum dot composition that does not contain a solvent while exhibiting low viscosity and good optical properties, and a method for preparing the same.

DISCLOSURE

Technical Problem

The prior inventions require use of separated and purified quantum dot powder for ligand substitution on surfaces of quantum dots in a preparation process thereof, as in the prior art. However, it was confirmed that at least two centrifugation processes were needed to separate and purify the prepared quantum dots, thereby making the process complicated while increasing preparation costs.

It is one aspect of the present invention to provide a solventless quantum dot composition and a method for preparing the same, in which a solution containing quantum dots synthesized therein is used for ligand substitution without a separation/purification process, such as centrifugation, thereby simplifying a preparation process and reducing costs while securing good optical efficiency and lower viscosity.

It is another aspect of the present invention to provide a cured film, a color filter and a display device including the solventless quantum dot composition.

Technical Solution

In accordance with one aspect of the present invention, there is provided a method for preparing a solventless quantum dot composition, including:
(a) synthesizing quantum dots;
(b) subjecting the quantum dots to primary surface modification with a primary ligand comprising an ethylene glycol structure without separating the quantum dots from a solution containing the quantum dots synthesized therein;
(c) subjecting the primary surface-modified quantum dots to secondary surface modification with a secondary ligand represented by Formula 1:

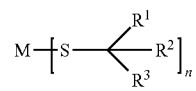

[Formula 1]

(In Formula 1,
M is a bivalent to tetravalent metal,
$R^1$ to $R^3$ are independently hydrogen or a $C_3$ to $C_{70}$ organic group, and
n is an integer of 2 to 4.)

(d) obtaining surface-modified quantum dots from a product of step (c); and (e) dispersing the obtained surface-modified quantum dots in a photopolymerizable monomer.

Preferably, the method further includes, after step (c), (f) subjecting the surface-modified quantum dots to tertiary surface modification by adding a $C_3$ to $C_{40}$ tertiary ligand containing a carboxyl group to the solution.

Preferably, the primary ligand has a molecular weight of 100 g/mol to 500 g/mol and includes 1 to 5 repeat units of the ethylene glycol structure.

Preferably, at least one of $R^1$ to $R^3$ in Formula 1 includes repeat units of the ethylene glycol structure,
the total number of repeat units of the ethylene glycol structure contained in $R^1$ to $R^3$ ranges from 2 to 15, and
a $C_1$ to $C_{15}$ organic group is bound to a terminal of the ethylene glycol structure.

Preferably, the tertiary ligand is represented by Formula 2.

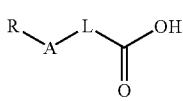

[Formula 2]

(In Formula 2,
L is a single bond or selected from the group consisting of substituted or unsubstituted $C_1$ to $C_{20}$ alkylene groups and substituted or unsubstituted $C_1$ to $C_{20}$ alkenylene groups,
A is a single bond or a C1 to C20 alkylene or alkenylene group containing at least one functional group selected from the group consisting of ester (—C(=O)O—), ether (—O—), carbonyl (—C(=O)—), sulfonyl (—SO$_2$—), sulfide (—S—), and sulfoxide (—SO—) groups, and
R is hydrogen or selected from the group consisting of substituted or unsubstituted $C_1$ to $C_{20}$ alkyl groups and substituted or unsubstituted $C_1$ to $C_{20}$ alkenyl groups).

Preferably, the quantum dots and the total ligands are mixed in a weight ratio of 1:1 to 1:20.

Preferably, the primary ligand and the secondary ligand added to the solution are present in a mole ratio of 1:1 to 1:20.

Preferably, the primary ligand, the secondary ligand and the tertiary ligand added to the solution are present in a mole ratio of 1:1-20 to 1:1-30.

Preferably, the primary ligand is at least one selected from the group consisting of methoxy triethylene glycol thioglycolate and 2-(2-methoxyethoxy)acetic acid.

Preferably, the secondary ligand is at least one selected from the group consisting of Zn-(3-methoxybutyl 3-mercaptopropionate)$_2$, Zn-(3-methoxybutyl thioglycolate)$_2$, Zn-(2-ethylhexyl thioglycolate)$_2$, Zn-(butyl mercaptopropionate)$_2$, Zn-(isopropyl mercaptopropionate)$_2$, Zn-(bis-(butoxy triethylene glycol)mercapto succinate)$_2$, and Zn-(poly(ethylene glycol)methyl ether-thioglycolate)$_2$.

Preferably, the tertiary ligand is at least one selected from the group consisting of 2-carboxyethyl acrylate, mono-2-(acryloyloxy)ethyl succinate, mono-2-(methacryloyloxy) ethyl succinate, mono-2-(methacryloyloxy)ethyl maleate, mono-2-(methacryloyloxy)ethyl maleate, 2-[2-(2-methoxyethoxy)ethoxy]acetic acid, 2-(2-methoxyethoxy)acetic acid, and 2-(2-methoxyethoxy)acetic acid.

Preferably, the solution includes at least one selected from the group consisting of fatty acids, fatty acid derivatives, by-products of quantum dot synthesis reaction, dioctyl octadecenamide, trioctylphosphine and oxides thereof, n-octadecene, trioctylamine, metal acetate, metal oleate, tris(trimethylsilyl)phosphine, selenium (Se), sulfur (S), selenium-trioctylphosphine, sulfur-trioctylphosphine, chloride salt, and metal chloride.

Preferably, the photopolymerizable monomer is 1,6-hexandiol diacrylate.

In accordance with another aspect of the present invention, there is provided a solventless quantum dot composition comprising:
quantum dots and a photopolymerizable monomer,
wherein the quantum dots are subjected to surface modification with a primary ligand comprising an ethylene glycol structure; and
a secondary ligand represented by Formula 1.

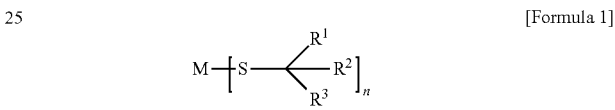

[Formula 1]

(In Formula 1,
M is a bivalent to tetravalent metal,
$R^1$ to $R^3$ are independently hydrogen or a $C_3$ to $C_{70}$ organic group, and
n is an integer of 2 to 4.)

Preferably, the surface-modified quantum dots are subjected to surface modification with a $C_3$ to $C_{40}$ tertiary ligand containing a carboxyl group.

Preferably, surface modification of the quantum dots is performed in a solution containing the quantum dots synthesized therein.

Preferably, the primary ligand has a molecular weight of 100 g/mol to 500 g/mol and includes 1 to 5 repeat units of the ethylene glycol structure.

Preferably, at least one of $R^1$ to $R^3$ in Formula 1 includes repeat units of the ethylene glycol structure,
the total number of repeat units of the ethylene glycol structure contained in $R^1$ to $R^3$ ranges from 2 to 15, and
a $C_1$ to $C_{15}$ organic group is bound to a terminal of the ethylene glycol structure.

Preferably, the tertiary ligand is represented by Formula 2.

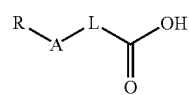

[Formula 2]

(In Formula 2,
L is a single bond or selected from the group consisting of substituted or unsubstituted $C_1$ to $C_{20}$ alkylene groups and substituted or unsubstituted $C_1$ to $C_{20}$ alkenylene groups,
A is a single bond or a $C_1$ to $C_{20}$ alkylene or alkenylene group containing at least one functional group selected from the group consisting of ester (—C(=O)O—), ether (—O—), carbonyl (—C(=O)—), sulfonyl (—SO$_2$—), sulfide (—S—), and sulfoxide (—SO—) groups, and R is hydrogen or selected from the group consisting of substituted or unsubstituted C$_1$ to C$_{20}$ alkyl groups and substituted or unsubstituted C$_1$ to C$_{20}$ alkenyl groups).

Preferably, the primary ligand includes at least one selected from the group consisting of methoxy triethylene glycol thioglycolate and 2-(2-methoxyethoxy)acetic acid.

Preferably, the secondary ligand includes at least one selected from the group consisting of Zn-(3-methoxybutyl 3-mercaptopropionate)$_2$, Zn-(3-methoxybutyl thioglycolate)$_2$, Zn-(2-ethylhexyl thioglycolate)$_2$, Zn-(butyl mercaptopropionate)$_2$, Zn-(isopropyl mercaptopropionate)$_2$, Zn-(bis-(butoxy triethylene glycol)mercapto succinate)$_2$, and Zn-(poly (ethylene glycol)methyl ether-thioglycolate)$_2$.

Preferably, the tertiary ligand includes at least one selected from the group consisting of 2-carboxyethyl acrylate, mono-2-(acryloyloxy)ethyl succinate, mono-2-(methacryloyloxy)ethyl succinate, mono-2-(methacryloyloxy) ethyl maleate, mono-2-(methacryloyloxy)ethyl maleate, 2-[2-(2-methoxyethoxy)ethoxy]acetic acid, 2-(2-methoxyethoxy)acetic acid, and 2-(2-methoxyethoxy)acetic acid.

Preferably, M is Mg, Ca, Sc, Ti, V, Cr, Mn, Fe, Co, Ni, Cu, Zn, Ga, Ge, Sr, Mo, Pd, Cd, In, or Sn.

Preferably, M is Zn.

Preferably, the primary ligand and the secondary ligand are present in a mole ratio of 1:1 to 1:20.

Preferably, the primary ligand, the secondary ligand and the tertiary ligand are present in a mole ratio of 1:1 to 1:1-20: 1-30.

Preferably, the quantum dots and the ligands are mixed in a weight ratio of 1:1 to 1:20.

Preferably, the photopolymerizable monomer is a (meth) acrylate monomer.

Preferably, the photopolymerizable monomer is 1,6-hexandiol diacrylate.

Preferably, the solventless quantum dot composition has a viscosity of 30 cP or less.

Preferably, the solventless quantum dot composition is used for inkjet printing.

Preferably, there is provided a cured film prepared using the solventless quantum dot composition.

Preferably, the cured film has an absolute quantum efficiency of 30% or more when the solventless quantum dot composition is coated to a thickness of 10±0.5 km.

Preferably, there is provided a color filter comprising the solventless quantum dot composition.

Preferably, there is provided a display device comprising the color filter.

Advantageous Effects

Conventionally, it is difficult to achieve surface modification of quantum dots by directly introducing a ligand into a solution containing a solvent for synthesis of quantum dots and residues thereof without separation/purification of the quantum dots from the solution through an additional process after the quantum dots are synthesized in the solution. However, the solventless quantum dot composition and the method for preparing the same according to the present invention allow surface modification of quantum dots directly in the corresponding solution, thereby simplifying the preparation process while reducing preparation costs.

The solventless quantum dot composition according to the present invention can exhibit good miscibility between quantum dots and monomers without a solvent. Furthermore, the solventless quantum dot composition according to the present invention exhibits good optical properties and low viscosity, and thus can be used for inkjet printing.

BEST MODE

Hereinafter, exemplary embodiments of the present disclosure will be described in detail.

Unless otherwise defined herein, all terms (including technical and scientific terms) used herein have the same meaning as commonly understood by one of ordinary skill in the art to which this disclosure pertains. Terms, such as those defined in commonly used dictionaries, should be interpreted as having a meaning that is consistent with their meaning in the context of the related art and should not be interpreted in an idealized or overly formal sense, unless clearly defined herein.

In addition, as used herein, the terms "comprises," "comprising," "includes," and/or "including" specify the presence of stated features, integers, steps, operations, elements, components, and/or groups thereof, but do not preclude the presence or addition of one or more other features, integers, steps, operations, elements, components, and/or groups thereof.

Further, as used herein, "(meth)acrylate" refers to acrylate and methacrylate, "(meth)acryl" refers to acryl and methacryl, and "(meth)acryloyl" refers to acryloyl and methacryloyl.

Further, as used herein, the terms "monomer" and "monomer" have the same meaning. In the context of the invention, a monomer is distinguished from oligomers and polymers and is a compound having a weight average molecular weight of 1,000 or less. Herein, "photopolymerizable monomer" refers to a functional group involved in polymerization reaction, for example, a (meth)acrylate group.

Herein, "substituted" means that a hydrogen in a compound or a functional group is substituted with a substituent selected from among a C$_1$ to C$_{30}$ alkyl group, a C$_2$ to C$_{30}$ alkenyl group, a C$_2$ to C$_{30}$ alkynyl group, a C$_1$ to C$_{30}$ alkoxy group, a C$_1$ to C$_{30}$ heteroalkyl group, a C$_3$ to C$_{30}$ heteroalkylaryl group, a C$_3$ to C$_{30}$ cycloalkyl group, a C$_3$ to C$_{15}$ cycloalkenyl group, a C$_6$ to C$_{30}$ cycloalkynyl group, a C$_2$ to C$_3$n heterocycloalkyl group, a halogen (—F, —Cl, —Br or —I), a hydroxyl group (—OH), a nitro group (—NO$_2$), a cyano group (—CN), an ester group (—C(=O)OR), R being a C$_1$ to C$_{10}$ alkyl or alkenyl group), an ether group (—O—R, R being a C$_1$ to C$_{10}$ alkyl or alkenyl group), a carbonyl group (—C(=O)—R, R being a C$_1$ to C$_{10}$ alkyl or alkenyl group), a carboxyl group (—COOH), and combinations thereof.

Herein, "organic group" means a C$_1$ to C$_{30}$ straight or branched alkyl group, C$_2$ to C$_{30}$ straight or branched chain alkenyl group, and a C$_2$ to C$_{30}$ straight or branched chain alkynyl group. In addition, each of the alkyl, alkenyl and alkynyl groups may be substituted or unsubstituted.

Herein, "alkyl" refers to a monovalent substituent group derived from a C$_1$ to C$_{40}$ straight or side chain saturated hydrocarbon. Examples of the alkyl group include a methyl group, an ethyl group, a propyl group, an isobutyl group, a sec-butyl group, a pentyl group, an iso-amyl group, a hexyl group, and the like, without being limited thereto.

Herein, "alkenyl" refers to a monovalent substituent group derived from a C$_{12}$ to C$_{40}$ straight or side chain unsaturated hydrocarbon having at least one carbon-carbon double bond. Examples of the alkenyl include a vinyl group, an allyl group, an isopropenyl group, and a 2-butenyl group, without being limited thereto.

<Solvent-Free Quantum Dot Composition>

A quantum dot composition according to one embodiment of the present invention is a solventless quantum dot composition. Specifically, the solventless quantum dot composition has low viscosity and good optical properties, and is applicable to inkjet printing, even without containing a solvent.

In some embodiments of the invention, there is provided a solventless quantum dot composition comprising quantum dots and a photopolymerizable monomer, wherein the quantum dots are subjected to surface modification with a primary ligand comprising an ethylene glycol structure and a secondary ligand represented by Formula 1.

In addition, there is provided a solventless quantum dot composition comprising quantum dots and a photopolymerizable monomer, wherein the quantum dots are subjected to surface modification with a primary ligand comprising an ethylene glycol structure, a secondary ligand represented by Formula 1, and a $C_3$ to $C_{40}$ tertiary ligand containing a carboxyl group.

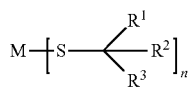

[Formula 1]

(In Formula 1,
M is a bivalent to tetravalent metal,
$R^1$ to $R^3$ are independently hydrogen or a $C_3$ to $C_{70}$ organic group, and
n is an integer of 2 to 4.)

Further, in the solventless quantum dot compositions, surface modification of the quantum dots may be carried out in a solution containing the quantum dots synthesized therein.

Hereinafter, components of the quantum dot composition will be described in detail.

Quantum Dot

Quantum dots (QDs) are nanoscale semiconductor materials that can have different energy bandgaps depending on the size and composition thereof and thus can emit light with various emission wavelengths.

The quantum dots may have a homogeneous monolayer structure, a multilayer structure, such as a core-shell structure, a gradient structure, and the like, or a mixture thereof. When the shell has a multilayer structure, each layer may contain a different component, for example, a (quasi-) metal oxide.

The quantum dots (QDs) may be freely selected from among a group II-VI compound, a group III-V compound, a group IV-VI compound, a group IV element, a group IV compound, and combinations thereof. When the quantum dots have a core-shell structure, each of the core and the shell may be freely selected from components exemplified below.

In one example, the group II-VI compound may be selected from the group consisting of a binary compound selected from the group consisting of CdO, CdS, CdSe, CdTe, ZnO, ZnS, ZnSe, ZnTe, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group consisting of CdZnSeS, CdZnSeTe, CdZnSTe, CdHgSeS, CdHgSeTe, CdHgSTe, HgZnSeS, HgZnSeTe, HgZnSTe, and mixtures thereof.

In another example, the group III-V compound may be selected from the group consisting of a binary compound selected from the group consisting of GaN, GaP, GaAs, GaSb, AlN, AlP, AlAs, AlSb, InN, InP, InAs, InSb, and mixtures thereof; a ternary compound selected from the group consisting of GaNP, GaNAs, GaNSb, GaPAs, GaPSb, AlNP, AlNAs, AlNSb, AlPAs, AlPSb, InNP, InNAs, InNSb, InPAs, InPSb, and mixtures thereof; and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof.

In another example, the group IV-VI compound may be selected from the group consisting of a binary compound selected from the group consisting of SnS, SnSe, SnTe, PbS, PbSe, PbTe, and mixtures thereof; a ternary compound selected from the group consisting of SnSeS, SnSeTe, SnSTe, PbSeS, PbSeTe, PbSTe, SnPbS, SnPbSe, SnPbTe, and mixtures thereof; and a quaternary compound selected from the group consisting of SnPbSSe, SnPbSeTe, SnPbSTe, and mixtures thereof.

In another example, the group IV element may be selected from the group consisting of Si, Ge, and mixtures thereof. The group IV compound may be a binary compound selected from the group consisting of SiC, SiGe, and mixtures thereof.

The aforementioned binary, ternary or quaternary compounds may be present in particles at a uniform concentration or may be present in the same particle with a partially different concentration distribution. Alternatively, the quantum dots may have a core/shell structure in which one quantum dot surrounds another quantum dot. An interface between the core and the shell may have a concentration gradient where the concentration of elements present in the shell gradually decreases toward the center.

The quantum dots may have any typical shape commonly used in the art. For example, the quantum dots may have a spherical shape, a rod shape, a pyramidal shape, a disc shape, a multi-armed shape, cubic nanoparticle, nanotube, nanowire, nanofiber, nano-platelet shapes, and the like.

Further, the size of the quantum dots is not particularly limited and may be adjusted within the range known to those skilled in the art. For example, the quantum dots may have an average particle diameter (D50) of about 2 nm to about 10 nm. In this way, when the particle diameter of the quantum dots is controlled in the range of about 2 nm to about 10 nm, the quantum dots can emit light of a desired color. For example, when the InP-containing quantum dot core/shell has a particle diameter of about 5 nm to 6 nm, the quantum dots can emit light with a wavelength of about 520 nm to about 550 nm, and when the InP-containing quantum dot core/shell has a particle diameter of about 7 nm to about 8 nm, the quantum dots can emit light with a wavelength of about 620 nm to about 640 nm. For example, non-cadmium (Cd) based group III-V quantum dots (for example, InP, InGaP, InZnP, GaN, GaAs, and GaP) may be used as blue light emitting quantum dots (QDs).

Further, the quantum dots may have a full width of half maximum (FWHM) of an emission wavelength spectrum of about 40 nm or less and can improve color purity or color reproduction within this range. In addition, light emitted from such quantum dots is emitted in all directions, thereby improving light viewing angle.

According to embodiments of the invention, the quantum dots may be present in an amount of 1 wt % to 60 wt %, preferably 20 wt % to 50 wt %, based on the total weight of the solventless quantum dot composition.

Ligands

In the solventless quantum dot composition according to the present invention, the ligands serve to modify the surfaces of the quantum dots. Since hydrophobic properties of the surfaces of the quantum dots provides a barrier to dispersion of the photopolymerizable monomer, miscibility of the quantum dots to the photopolymerizable monomer can be improved through surface modification of the quantum dots with suitable ligands.

According to one embodiment of the invention, the ligands may include a primary ligand comprising an ethylene glycol structure and a secondary ligand represented by Formula 1.

According to one embodiment of the invention, the ligands may include a primary ligand comprising an ethylene glycol structure, a secondary ligand represented by Formula 1, and a $C_3$ to $C_{40}$ tertiary ligand containing a carboxyl group.

The primary ligand is introduced into the solution containing the quantum dots synthesized therein and promotes primary modification of the surface of the quantum dots, which exhibits hydrophobic properties, such that the surface of the quantum dots becomes slightly polarized, while facilitating subsequent substitution of the secondary and tertiary ligands in the solution containing generally hydrophobic quantum dots synthesized therein.

[Formula 1]

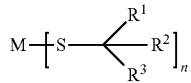

In Formula 1, M is a bivalent to tetravalent metal, $R^1$ and $R^3$ are independently hydrogen or a $C_3$ to $C_{70}$ organic group, and n is an integer of 2 to 4.

Typically, since a solvent (for example, 1-octadecene, n-octadecene, trioctyl amine, and the like) used in preparation of the quantum dots exhibits hydrophobic properties and the solution containing the quantum dots synthesized therein contains various synthesis residues (for example, fatty acids such as oleic acid and the like, fatty acid derivatives such as octyl oleate and the like, other byproducts such as dioctyl octadecenamide and the like, trioctyl phosphine and oxides thereof, solvents such as n-octadecene or trioctyl amine, metal acetate, metal oleate, tris(trimethylsilyl)phosphine, Se, S, Se-trioctyl phosphine, S-trioctyl phosphine, chloride salt, metal chloride, and the like), it is difficult to achieve direct surface modification of the quantum dots with most ligands including metal-thiol based ligands without separating and purifying the quantum dots from the solution. However, in one embodiment of the invention, after the quantum dots are modified with the primary ligand including the ethylene glycol structure in the solution containing the quantum dots synthesized therein, surface modification with other ligands including metal-thiol based ligands can be easily achieved even in the solution containing residual impurities after synthesis of the quantum dots.

The primary ligand may have a molecular weight of 100 g/mol to 500 g/mol, more preferably 100 g/mol to 500 g/mol, and may include 1 to 5 repeat units of the ethylene glycol structure. Specifically, the primary ligand may include at least one selected from the group consisting of methoxy triethylene glycol thioglycolate (hereinafter, MTEGT) and 2-(2-methoxyethoxy)acetic acid (hereinafter, MEAA), preferably MTEGT. An excessively large molecular weight of the primary ligand can be unfavorable for primary surface modification.

The secondary ligand may be a metal-thiol based compound prepared by reacting a metal salt with a thiol-based compound.

In the secondary ligand, M is a bivalent to tetravalent metal. For example, M is a group II to XIV metal and may be Mg, Ca, Sc, Ti, V, Cr, Mn, Fe, Co, Ni, Cu, Zn, Ga, Ge, Sr, Y, Zr, Nb, Mo, Tc, Ru, Rh, Pd, Cd, In, or Sn, preferably Zn. In Formula 1, n is determined by the valence number of M and is an integer of 2 to 4.

In Formula 1 representing the secondary ligand, at least one of R1 to R3 may include repeat units of the ethylene glycol structure, in which the total number of repeat units of the ethylene glycol structure in $R^1$ to $R^3$ ranges from 2 to 15 and a $C_1$ to $C_{15}$ organic group is bound to a terminal of the ethylene glycol structure.

In addition, at least one of $R^1$ to $R^3$ in Formula 1 may be a $C_3$ to $C_{20}$ organic group. For example, at least one of $R^1$ to $R^3$ may be a $C_3$ to $C_{20}$ alkylene or alkenylene group comprising at least one functional group selected from the group consisting of ester (—C(=O)O—), ether (—O—), carbonyl (—C(=O)—), carboxyl (—C(=O)—OH), sulfonyl (—SO$_2$—), sulfide (—S—), sulfoxide (—SO—), alkoxy ($C_nH_{2n+1}$O—), and hydroxyl (—OH) groups. Specifically, $R^1$ may be a $C_{14}$ to $C_{15}$ organic group comprising an ester (—C(=O)O—) functional group and $R^2$ and $R^3$ may be hydrogen.

In the secondary ligand, the thiol group has good affinity with the surfaces of the quantum dots, thereby improving dispersibility of the quantum dots with respect to the photopolymerizable monomer. In addition, the secondary ligand may include not only the thiol group, but also an ester group, an ether group, a carbonyl group, a carboxyl group, an alkoxy group, a cycloalkyl group, or a hydroxyl group, thereby maximizing dispersibility of the surface modified quantum dots with respect to a polar monomer exhibiting hydrophobic properties. Furthermore, the quantum dot composition comprising such quantum dots may have properties (for example, low viscosity) favorable for display processes. On the other hand, although a thiol-based compound having a carbon number of 3 or less allows surface modification of the quantum dots, high polarity of the surface modified quantum dots can cause difficulty in dispersion of the quantum dots in common solvents and monomers.

Specifically, the secondary ligand may include at least one selected from the group consisting of Zn-(3-methoxybutyl 3-mercaptopropionate)$_2$, Zn-(3-methoxybutyl thioglycolate)$_2$, Zn-(2-ethylhexyl thioglycolate)$_2$, Zn-(butyl mercaptopropionate)$_2$, Zn-(isopropyl mercaptopropionate)$_2$, Zn-(Bis-(butoxy triethylene glycol)mercapto succinate)$_2$ and Zn-(poly(ethylene glycol)methyl ether-thioglycolate)$_2$.

The tertiary ligand may have a carbon number of 3 to 40 and may include a carboxyl group. In addition, according to one embodiment of the invention, the tertiary ligand may not contain a thiol group.

According to one embodiment of the invention, the tertiary ligand may be represented by Formula 2.

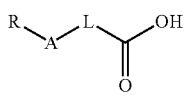 [Formula 2]

In Formula 2,
L is a single bond or selected from the group consisting of substituted or unsubstituted $C_1$ to $C_{20}$ alkylene groups and substituted or unsubstituted $C_1$ to $C_{20}$ alkenylene groups,
A is a single bond or a $C_1$ to $C_{20}$ alkylene or alkenylene group containing at least one functional group selected from the group consisting of ester (—C(=O)O—), ether (—O—), carbonyl (—C(=O)—), sulfonyl (—SO$_2$—), sulfide (—S—), and sulfoxide (—SO—) groups, and
R is hydrogen or selected from the group consisting of substituted or unsubstituted $C_1$ to $C_{20}$ alkyl groups and substituted or unsubstituted $C_1$ to $C_{20}$ alkenyl groups.

Preferably, A in the tertiary ligand may include an ester group (—COO—), an ether group (—O—), or a combination thereof. Further, A may be a $C_2$ to $C_{15}$ alkylene or alkenylene group, preferably a $C_2$ to $C_{10}$ alkylene or alkenylene group.

Specifically, the tertiary ligand may be at least one selected from the group consisting of 2-carboxyethyl acrylate, mono-2-(acryloyloxy)ethyl succinate, mono-2-(methacryloyloxy)ethyl succinate, mono-2-(methacryloyloxy)ethyl maleate, 2-[2-(2-methoxyethoxy)ethoxy]acetic acid, and 2-(2-methoxyethoxy)acetic acid.

In general, thiol-based ligands are known to be highly reactive with the surface of the quantum dot. However, quantum dot compositions comprising only the thiol-based ligands are unsuitable for use in inkjet compositions due to generation of toxic odor (gas) or increase in viscosity causing poor storage stability. The quantum dot composition according to the present invention exhibits low viscosity and good storage stability (degree of change in QE value before and after heat treatment) through use of the secondary ligand comprising a thiol-based ligand and the tertiary ligand not containing a thiol group together. In addition, the tertiary ligands contains a functional group, such as an ester group (—C(=O)O—), an ether group (—O—), a carbonyl group (—C(=O)—), a carboxyl group (—C(=O)—OH), and the like, thereby securing good dispersibility in the photopolymerizable monomer. On the other hand, when the tertiary ligand has a carbon number of 16 or more, there can be a problem, such as failure in surface modification of the quantum dots or deterioration in dispersibility in common solvents and monomers.

When both the primary ligand and the secondary ligand repeatedly include the ethylene glycol structure, an ink composition can exhibit better viscosity and optical properties than when both the primary ligand and the secondary ligand do not repeatedly include the ethylene glycol structure. It is believed that this phenomenon is caused by further improvement in dispersion of QDs in the composition due to strong hydrophilic properties of the ethylene glycol structure.

According to one embodiment of the invention, the primary ligand and the secondary ligand may be present in a mole ratio of 1:1 to 1:20, preferably 1:1 to 1:10, more preferably 1:1 to 1:5, without being limited thereto.

In addition, according to one embodiment of the invention, the first ligand, the second ligand and the tertiary ligand may be present in a mole ratio of 1:1 to 20:1 to 30, preferably 1:1 to 10:1 to 15, more preferably 1:1 to 5:1 to 8, without being limited thereto.

Furthermore, according to one embodiment of the invention, the quantum dots and the ligand may be mixed in a weight ratio of 1:1 to 20, preferably 1:1 to 10, more preferably 1:5 to 10. Here, the ligand means the sum of the primary ligand and the secondary ligand, or the sum of the primary ligand, the secondary ligand and the tertiary ligand.

Photopolymerizable Monomer

In the quantum dot compositions according to the present invention, the photopolymerizable monomer serves to control a formulation in which the quantum dots (QDs) are dispersed, that is, an overall crosslinking density of a polymer matrix, thereby realizing the structure and other properties of the matrix. In addition, the photopolymerizable monomer can improve flexibility and adhesion to other materials.

The photopolymerizable monomer may include a (meth)acrylate monomer. The monomer may be any typical monomer used in the art without limitation.

By way of example, the (meth)acrylate monomer may include at least one of a (meth)acrylic group, a vinyl group, and an allyl group. Specifically, the (meth)acrylate monomer may include 1,6-hexanediol diacrylate, 1,6-cyclohexanediol diacrylate, 2,2-dimethyl-1,3-propanediol diacrylate, and diethylene glycol diacrylate, dipropylene glycol diacrylate, 1,3-butylene glycol dimethacrylate, trimethylolpropane trimethacrylate, isobornyl acrylate, and isobornyl methacrylate, tetrahydrofuryl acrylate, acryloyl morpholine, 2-phenoxyethyl acrylate, tripropylene glycol diacrylate, trimethylolpropane triacrylate, pentaerythritol mono(meth)acrylate, pentaerythritol di(meth)acrylate, pentaerythritol triacrylate, pentaerythritol trimethacrylate, dipentaerythritol hexaacrylate, dipentaerythritol hexamethacrylate, and the like. These may be used alone or as a mixture thereof. In the present invention, the photopolymerizable monomer may be 1,6-hexanediol diacrylate to achieve viscosity properties of the solventless quantum dot composition.

According to the present invention, the (meth)acrylamide-based monomer may be present in an amount of 35 wt % to 80 wt %, preferably 45 wt % to 70 wt %, based on the total weight of the solventless quantum dot composition.

Photo-Initiator

In the solventless quantum dot composition according to the present invention, the photo-initiator serves to initiate photopolymerization by being excited by light, such as ultraviolet (UV) light, and may be selected from typical photopolymerizable initiators in the art without limitation. For example, the photo-initiator may be selected from among acetophenone compounds, benzophenone compounds, thioxanthone compounds, benzoin compounds, triazine compounds, oxime compounds, and the like.

Examples of the photo-initiators may include ethyl(2,4,6-trimethylbenzoyl)phenyl phosphinate, Irgacure 184, Irgacure 369, Irgacure 651, Irgacure 819, Irgacure 907, benzoin alkyl ether, benzophenone, benzyl dimethyl ketal, hydroxycyclohexyl phenyl acetone, chloroacetophenone, 1,1-dichloro acetophenone, diethoxy acetophenone, hydroxy acetophenone, 2-chlorothioxanthone, 2-ETAQ (2-ethyl anthraquinone), 1-hydroxy-cyclohexyl-phenyl-ketone, 2-hydroxy-2-methyl-1-phenyl-1-propanone, 2-hydroxy-1-[4-(2-hydroxyethoxy)phenyl]-2-methyl-1-propanone, and methyl benzoyl formate, without being limited thereto. These may be used alone or as a mixture thereof.

The content of the photo-initiator may be suitably adjusted within the range known in the art. For example, the photo-initiator may be present in an amount of 0.01 wt % to 10 wt %, preferably 0.1 wt % to 5 wt %, based on the total weight of the solventless quantum dot composition. Within this range, the photo-initiator can secure sufficient photopolymerization reaction without degradation in properties of the matrix.

Diffusing Agent

In the solventless quantum dot composition according to the present invention, the diffusing agent reflects light not absorbed by a photo-conversion material and allows the photo-conversion material to reabsorb the reflected light. That is, the diffusing agent can increase the quantity of light absorbed by the photo-conversion material, thereby improving light conversion efficiency.

The diffusing agent may be any type of diffusing agent component known in the art, without limitation. The diffusing agent may be prepared in the form of a solid, such as powder, or a dispersion in which the diffusing agent is dispersed.

Examples of the diffusing agent may include barium sulfate ($BaSO_4$), calcium carbonate ($CaCO_3$), titanium dioxide ($TiO_2$), zirconia ($ZrO_2$), or combinations thereof, without being limited thereto. Furthermore, the average particle size or shape of the diffusing agent is not particularly limited and may be suitably selected, as known in the art. For example, the diffusing agent may have an average particle diameter (D50) of 150 nm to 250 nm, particularly 180 nm to 230 nm. Within this range, the diffusing agent can secure better light diffusion while improving light conversion efficiency.

The content of the diffusing agent may be suitably adjusted within the range known in the art. For example, the diffusing agent may be present in an amount of 0.01 wt % to 10 wt %, preferably 0.1 wt % to 5 wt %, based on the total weight of the solventless quantum dot composition. Within this range, the diffusing agent can secure improvement in light conversion efficiency without degradation in properties of the matrix.

Polymerization Inhibitor

In the solventless quantum dot composition according to the present invention, the polymerization inhibitor forms a low-reactivity radical or compound, which cannot cause polymerization reaction, through reaction with radicals and can adjust a photopolymerization reaction rate.

The polymerization inhibitor may be any type of polymerization inhibitor known in the art. For example, the polymerization inhibitor may include quinone compounds, phenol or aniline compounds, and aromatic nitro and nitroso compounds. Specifically, the polymerization inhibitor may include hydroquinone (HQ), methyl hydroquinone (THQ), hydroquinone monomethyl ether (MEHQ) and hydroquinone monoethyl ether (EEHQ) 1,4-benzoquinone (BQ), 2,5-diphenylbenzoquinone (DPBQ), methyl-1,4-benzoquinone (MBQ), phenyl-1,4-benzoquinone (PBQ); 2,6-di-tert-butyl-4-methylphenol (BHT), 2,6-diphenyl-4-octadecyloxyphenol, catechol; phenothiazines, bis($\alpha$-methylbenzyl) phenothiazine, 3,7-dioctylphenothiazine, bis($\alpha,\alpha$-dimethylbenzyl)phenothiazine; dimethyl dithiocarbamic acid, diethyl dithiocarbamic acid, dipropyl dithiocarbamic acid, dibutyl dithiocarbamic acid, diphenyl dithiocarbamic acid, and the like. These may be used alone or as a mixture thereof.

The content of the polymerization inhibitor may be suitably adjusted within the range known in the art. For example, the polymerization inhibitor may be present in an amount of 0.01 wt % to 2 wt %, preferably 0.05 wt % to 1 wt %, based on the total weight of the solventless quantum dot composition.

Stabilizer

In the solventless quantum dot composition according to the present invention, the stabilizer serves to improve stability and dispersibility of the quantum dots. The stabilizer may be substituted onto the shell surfaces of the quantum dots to stabilize the quantum dots through improvement in dispersion stability of the quantum dots in the solvent.

The stabilizer may be any type of substance known in the art that can improve stability and dispersibility of the quantum dots and may be, for example, a thiol-based stabilizer. The thiol-based stabilizer can improve dispersibility of the quantum dots with respect to the photopolymerizable monomer. In addition, a thiol group in the thiol-based stabilizer can react with an acryl group of the photopolymerizable monomer to form a covalent bond, thereby improving heat resistance of the quantum dot composition.

The thiol-based stabilizer may have 7 or more carbon atoms and may have 2 to 10, for example, 2 to 6, thiol groups (—SH) at terminals thereof depending on the structure thereof, without being limited thereto. Examples of the thiol-based stabilizer may include pentaerythritol tetrakis(3-mercaptopropionate)trimethylolpropane tris(3-mercaptopropionate), pentaerythritol tetrakis(mercaptoacetate), trimethylolpropane tris(2-mercaptoacetate), glycol di-3-mercaptopropionate, or mixtures thereof.

Other Additives

In addition to the aforementioned components, the quantum dot composition according to the present invention may include any additives known in the art without limitation within the range not affecting effectiveness of the quantum dot composition. Here, the content of the additives may be suitably adjusted within the range known in the art.

Examples of the additives include a silane compound, a siloxane compound, an antioxidant, a polymerization inhibitor, a lubricant, a surface modifier, surfactants, an adhesion enhancer, a defoaming agent, a slip agent, a solvent, a wetting agent, a light stabilizer, a stain inhibitor, a softener, a thickener, a polymer, and the like. These additives may be used alone or as a mixture thereof.

The silane compound serves to impart adhesion to the matrix and the siloxane compound serves to impart wettability. The silane compound and the siloxane compound may be selected from typical compounds known in the art.

The antioxidant serves to inhibit discoloration by heat or light irradiation and discoloration due to various oxidizing gases, such as ozone, reactive oxygen species, NOx, SOX (where X is an integer), and the like. In the present invention, the antioxidant can prevent discoloration of the matrix or can suppress reduction in film thickness due to degradation. Examples of the antioxidant include hydrazides, hindered amine antioxidants, nitrogen complex-ring mercapto compounds, thioether antioxidants, hindered phenol antioxidants, ascorbic acid, zinc sulfate, thiocyanates, thiourea derivatives, sugars, nitrites, sulfites, thiosulfates, hydroxylamine derivatives, and the like.

The leveling agent may be used to further enhance adhesion of the composition by leveling the quantum dot composition such that that the quantum dot composition can be coated flatly and evenly. The leveling agent may include an acrylic compound, a silicone compound, or a mixture thereof. For example, the leveling agent may include polyether-modified polydimethylsiloxane containing a (meth)acryloyl group added to the polyether chain thereof.

The surfactant may be used for mixing and coating uniformity of the quantum dot composition. The surfactant may be selected from among typical cationic, anionic and non-ionic surfactants known in the art. For example, the surfactant may include at least one of a fluorinated surfactant, a silicone surfactant, and a fluorosilicone surfactant.

The light stabilizer is a UV absorbent and has an effect of increasing weather resistance of the matrix. The softener serves to mitigate occurrence of cracks in the dried polymer matrix and can improve impact resistance and flexural resistance by mitigating occurrence of cracks in a cured matrix.

The solventless quantum dot composition according to the present invention includes quantum dots subjected to surface modification with two or more ligands and a photopolymerizable monomer having good miscibility with the ligand-substituted quantum dots.

The solventless quantum dot composition according to the present invention has good optical properties including a light absorption rate and a light change rate, and can realize low viscosity. Specifically, the solventless quantum dot composition may have a viscosity at room temperature (25° C.) of 30 cP or less, preferably 28 cP or less, more preferably 25 cP or less. Within this range of viscosity, the solventless quantum dot composition can exhibit not only good workability and processability, but also good storage stability at high temperature. Furthermore, the solventless quantum dot composition according to the present invention can realize low viscosity and thus can be used for inkjet printing.

<Method for Preparing Solventless Quantum Dot Composition>

In one embodiment of the present invention, a method for preparing a solventless quantum dot composition includes (a) synthesizing quantum dots; (b) subjecting the quantum dots to primary surface modification with a primary ligand comprising an ethylene glycol structure without separating the quantum dots from a solution containing the quantum dots synthesized therein; (c) subjecting the primary surface-modified quantum dots to secondary surface modification with a secondary ligand represented by Formula 1, (d) obtaining surface-modified quantum dots from a product of step (c); and (e) dispersing the obtained surface-modified quantum dots in a photopolymerizable monomer.

[Formula 1]

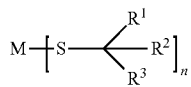

(In Formula 1,

M is a bivalent to tetravalent metal, $R^1$ to $R^3$ are independently hydrogen or a $C_3$ to $C_{70}$ organic group, and n is an integer of 2 to 4.)

The method may further include, after step (c), (f) subjecting the surface-modified quantum dots to tertiary surface modification by adding a $C_3$ to $C_{40}$ tertiary ligand containing a carboxyl group to the solution.

Modification of the quantum dots by the secondary ligand in step (c) is preferably performed after modification of the quantum dots with the primary ligand.

Here, the quantum dots, the primary ligand, the secondary ligand, the tertiary ligand, and the photopolymerizable monomer are the same as those described above. Furthermore, a quantum dot preparation method may be any method known in the art (for example, a hot injection method, a microfluidic reactor method, a method using microwave irradiation, and the like). Since the present invention is characterized in compositions of the ligands in the quantum dot synthesis solution and modification methods thereof rather than the quantum dot preparation method, the following description will focus on these features.

Specifically, step (b) may be the step of subjecting the quantum dots to primary surface modification by adding a solution of the primary ligand diluted to 20 wt % in cyclohexyl acetate to the solution containing the quantum dots synthesized therein, followed by stirring for about 5 hours, with the temperature of the solution containing the quantum dots therein lowered and maintained at about 80° C. In addition, step (c) may be the step of subjecting the quantum dots to secondary surface modification by adding a solution of the secondary ligand diluted to 20 wt % in cyclohexyl acetate to the solution containing the quantum dots therein, followed by stirring for about 90 minutes, with the temperature of the solution containing the quantum dots therein lowered to about 30° C. In addition, after step (c), the method may include the step of modifying the surfaces of the quantum dots by adding the tertiary ligand to the solution containing the quantum dots synthesized therein to react with the quantum dots for 30 minutes to 3 hours, with the temperature of the solution containing the quantum dots therein reduced again to about 30° C. by cooling the solution.

The step of surface modification of the quantum dots may be divided into two or three steps to prevent formation of by-products due to reaction between the primary ligand, the secondary ligand and the tertiary ligand, and the primary ligand is allowed to first react with the hydrophobic quantum dots to reduce hydrophobicity such that reaction with the secondary ligand and the tertiary ligand proceeds even in the solution for synthesis of the hydrophobic quantum dots, thereby enabling surface modification of the quantum dots while improving dispersibility of the quantum dots in the photopolymerizable monomer thereafter.

On the other hand, when the secondary and tertiary ligands are simultaneously introduced into the quantum dots, by-products can be formed due to thiol-ene reaction between the thiol group of the secondary ligand and an acrylate of the tertiary ligand. These by-products can improve viscosity of the quantum dot composition when the surface-modified quantum dots are dispersed in the photopolymerizable monomer.

In addition, the step of surface modification of the quantum dot may be a step of modifying the surface of the quantum dots by simultaneously introducing the secondary ligand and the tertiary ligand into the quantum dots subjected to primary surface modification to react therewith at 25° C. to 100° C. for 30 minutes to 3 hours.

After surface modification of the quantum dots by the method described above, the surface-modified quantum dots may be obtained through centrifugation. In addition, the solventless quantum dot composition may be prepared by dispersing the obtained quantum dots in a polymer monomer.

<Cured Film, Color Filter and Display Device>

The present invention may provide a cured film including the solventless quantum dot composition described above. The cured film according to the present invention may have good optical properties, specifically a light absorption rate of 75% or more, preferably 78% or more. In addition, the cured film may have a light conversion rate of 25% or more, more particularly 29% or more. Further, when coated to a thickness of 10±0.5 m, the cured film may have an absolute quantum efficiency of 30% or more.

The cured film may be produced by applying the solventless quantum dot composition described above to a substrate to form a pattern thereon by an inkjet printing method; and curing the pattern.

The present invention provides a color filter comprising the solventless quantum dot composition described above. The color filter is an optical component in the form of a thin film that extracts three colors, that is, red, green, and blue, in each pixel from white light emitted from a backlight source to allow a liquid crystal display to realize various colors.

Such a color filter may be manufactured by methods, such as dyeing, pigment dispersion, printing, and electrodeposition. In addition, the color filter including the quantum dot composition may be manufactured by an inkjet method. The inkjet method can prevent unnecessary waste of materials since the materials are used only for desired pixels.

The present invention also provides a display device comprising the aforementioned quantum dot composition. The display device includes a liquid crystal display (LCD), an electroluminescent display (EL), a plasma display (PDP), a field-emission display (FED), an organic light emitting diode (OLED) display, and the like without being limited thereto.

Next, the present invention will be described in more detail with reference to some examples. It should be understood that these examples are provided for illustration only and are not to be construed in any way as limiting the invention.

Synthesis Example of a Quantum Dot (QD)

1) In a 200 ml flask, zinc acetate and oleic acid were dissolved in 1-octadecene to prepare a solution, which in turn was heated to about 120° C. under vacuum and then cooled to room temperature to prepare a zinc oleate solution.
2) In a reaction flask, indium acetate and lauric acid were heated together with the zinc oleate solution to about 120° C. under vacuum. The mole ratio of indium to lauric acid was about 1:3. After about 1 hour, the atmosphere in the reactor was replaced by nitrogen. While the temperature in the reaction flask was raised to about 250° C., a mixed solution of tris(trimethylsilyl)phosphine ($TMS_3P$) and trioctylphosphine (hereinafter referred to as TOP), and, optionally, the zinc oleate solution, were rapidly injected into the reactor. During reaction, an indium oleate solution, a mixed solution of $TMS_3P$, and zinc oleate were sequentially injected into the reaction flask. The total reaction time was set to about 30 minutes.
3) An Se/TOP solution was prepared by dispersing Se in TOP at about 120° C. In addition, an S/TOP solution was prepared by dispersing S in TOP.
4) Zinc acetate and oleic acid were dissolved in trioctylamine (TOA) in a 300 mL reactor, followed by vacuum treatment at about 120° C. for about 10 minutes to prepare a zinc precursor. After replacing nitrogen (N2) in the flask, the temperature was raised to about 280° C. and was maintained for a predetermined period of time.
5) The prepared InZnP core and the prepared Se/TOP were added in a predetermined ratio and then heated to a high temperature of about 300° C. or more to form a ZnSe-containing layer through reaction therebetween.
6) When the Se precursor was exhausted, S/TOP and about 0.07 mmol of ZnCl2 were simultaneously introduced into the reactor. A ZnS-containing layer was formed through reaction for 1 hour.
7) InZnP/ZnSe/ZnS (core/shell/shell) quantum dots were prepared. As a final product, a solution containing the quantum dots dispersed in a hydrophobic TOA solvent and impurities, such as reaction residues (oleic acid, TOP, and the like), was obtained.

[Preparative Example 1] Preparation of Primary Ligand 1) 0.271 mol of thioglycolic acid, 0.276 mol of triethylene glycol monomethyl ether, and 0.027 mol of p-toluene sulfonic acid monohydrate (catalyst) were mixed in 350 ml of cyclohexane and reacted at about 80° C. under a nitrogen environment for about 18 hours.
2) After completion of reaction, cyclohexane was removed from the reaction product, which in turn was dissolved in chloroform.
3) The reaction product was neutralized with an aqueous solution of $NaHCO_3$, followed by removal of impurities therefrom using MgSO4.
4) Methoxy triethylene glycol thioglycolate (hereafter referred to as MTEGT or primary ligand) was prepared by removing the remaining solvent.

[Preparative Example 2-1] Preparation of Secondary Ligand 2-1

1) 0.271 mol of mercaptosuccinic acid, 0.276 mol of triethylene glycol butyl ether, and 0.027 mol of p-toluene sulfonic acid monohydrate (catalyst) were mixed in 350 ml of cyclohexane and reacted at about 80° C. nitrogen for about 18 hours under a nitrogen environment.
2) After completion of reaction, cyclohexane was removed from the reaction product, which in turn was dissolved in chloroform.
3) The reaction product was neutralized with an aqueous solution of $NaHCO_3$, followed by removal of impurities therefrom using MgSO4.
4) Bis-(butoxy triethylene glycol)mercaptosuccinate (hereinafter referred to as BTEGMS) was prepared by removing the remaining solvent.
5) $ZnCl_2$ and BTEGMS were reacted in a mole ratio of about 1:3 to prepare $Zn\text{-}(BTEGMS)_2$ as secondary ligand 2-1.

[Preparative Example 2-2] Preparation of Secondary Ligand 2-2

1) 0.271 mol of thioglycolic acid, 0.276 mol of poly(ethylene glycol)methyl ether 550 (water average molecular weight 550 g/mol), and 0.027 mol of p-toluene sulfonic acid monohydrate were mixed in 350 ml of cyclohexane and reacted at about 80° C. under a nitrogen environment for about 18 hours.
2) After completion of reaction, cyclohexane was removed from the reaction product, which in turn was dissolved in chloroform.
3) The reaction product was neutralized with an aqueous solution of $NaHCO_3$, followed by removal of impurities therefrom using MgSO4

4) PEG 550-thioglycolate (hereafter referred to as PEG550-T) was prepared by removing the remaining solvent.
5) ZnCl$_2$ and PEG550-T were reacted in a mole ratio of about 1:3 to prepare Zn-(PEG550-T)$_2$ as secondary ligand 2-2.

[Preparative Example 2-3] Preparation of Secondary Ligand 2-3

In a round bottom flask, zinc chloride (ZnCl$_2$) and a compound represented by Formula A-1 were added in a mole ratio of about 1:3 to cyclohexyl acetate, and were dissolved therein through thermal stirring at about 60° C. Secondary ligand 2-3 was prepared by removing HCl from the resulting solution under vacuum for about 2 hours.

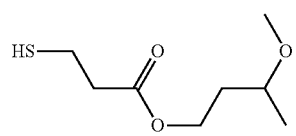

[A-1]

[Preparative Example 2-4] Preparation of Secondary Ligand 2-4

Secondary ligand 2-4 was prepared in the same manner as in Preparative Example 2-3 except that a compound represented by Formula A-2 was used instead of the compound represented by Formula A-1.

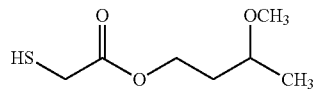

[A-2]

[Preparative Example 2-5] Preparation of Secondary Ligand 2-5

Secondary ligand 2-5 was prepared in the same manner as in Preparation Example 2-3 except that a compound represented by Formula A-3 was used instead of the compound represented by Formula A-1.

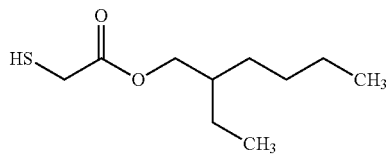

[A-3]

[Preparative Example 2-6] Preparation of Secondary Ligand 2-6

Secondary ligand 2-6 was prepared in the same manner as in Preparative Example 2-3 except that a compound represented by Formula A-4 was used instead of the compound represented by Formula A-1.

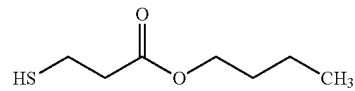

[A-4]

[Preparative Example 2-7] Preparation of Secondary Ligand 2-7

Secondary ligand 2-7 was prepared in the same manner as in Preparative Example 2-3 except that a compound represented by Formula A-5 was used instead of the compound represented by Formula A-1.

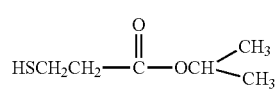

[A-5]

[Preparative Example 3-1] Preparation of Tertiary Ligand 3-1

In a round bottom flask, a compound represented by Formula B-1 was diluted to 20 wt % in cyclohexyl acetate, followed by stirring at room temperature for about 1 hour, thereby preparing tertiary ligand 3-1.

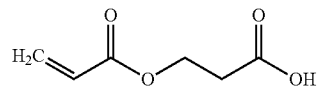

[B-1]

[Preparative Example 3-2] Preparation of Tertiary Ligand 3-2

Tertiary ligand 3-2 was prepared in the same manner as in Preparative Example 3-1 except that a compound represented by Formula B-2 was used instead of the compound represented by Formula B-1 in Preparative Example 3-1.

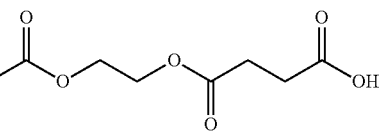

[B-2]

[Preparative Example 3-3] Preparation of Tertiary Ligand 3-3

Tertiary ligand 3-3 was prepared in the same manner as in Preparative Example 3-1 except that a compound represented by Formula B-3 was used instead of the compound represented by Formula B-1 in Preparative Example 3-1.

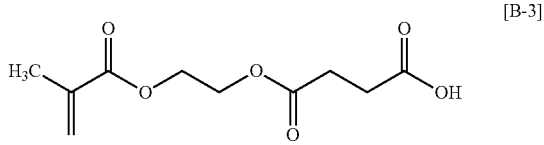 [SMILES: C=C(C)C(=O)OCCOC(=O)CCC(=O)O]

[Preparative Example 3-4] Preparation of Tertiary Ligands 3-4

Tertiary ligand 3-4 was prepared in the same manner as in Preparative Example 3-1 except that a compound represented by Formula B-4 was used instead of the compound represented by Formula B-1 in Preparative Example 3-1.

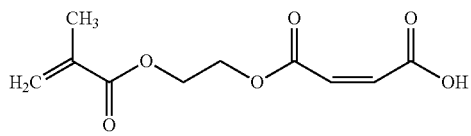

[Preparative Example 3-5] Preparation of Tertiary Ligand 3-5

Tertiary ligand 3-5 was prepared in the same manner as in Preparative Example 3-1 except that a compound represented by Formula B-5 was used instead of the compound represented by Formula B-1 in Preparative Example 3-1.

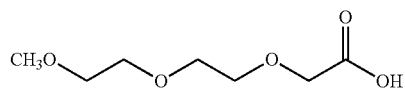

[Preparative Example 3-6] Preparation of Tertiary Ligand 3-6

Tertiary ligand 3-6 was prepared in the same manner as in Preparative Example 3-1 except that a compound represented by Formula B-6 was used instead of the compound represented by Formula B-1 in Preparative Example 3-1.

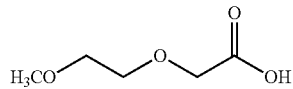

<Example 1> Preparation of Quantum Dot Composition 1-1. Preparation of Quantum Dots InZnP/ZnSe/ZnS quantum dots were synthesized as in the above preparative example of synthesizing QDs. A process of separating and purifying the quantum dots from a solution containing the quantum dots synthesized therein was not carried out.

1-2. Surface Modification of Quantum Dots

1) With the temperature of the solution (about 300 g) containing the synthesized quantum dots therein maintained at about 80° C., 6.2 g of a solution of MTEGT (primary ligand) prepared in Preparative Example 1 and diluted to 20 wt % in cyclohexyl acetate was added to the solution, which in turn was stirred for about 5 hours to subject the quantum dots to primary surface modification.

2) The temperature of the solution containing the quantum dots subjected to primary surface modification was reduced to about 30° C. and 0.8 g of a solution of secondary ligand 2-1 (Zn-(BTEGMS)$_2$) prepared in Preparative Example 2-1 and diluted to 20 wt % in cyclohexyl acetate was added to the solution, which in turn was stirred for about 90 minutes to subject the quantum dots to secondary surface modification.

3) Reaction was terminated by cooling the solution to room temperature.

1-3. Preparation of Quantum Dot-Monomer Dispersion

1) The solution containing the surface-modified quantum dots was subjected to centrifugation with hexane and acetone to prepare quantum dot powder.

2) QD dispersion 1 was prepared by dispersing 50 wt % of the quantum dot powder in 1,6-hexanediol diacrylate.

1-4. Preparation of QD Ink Composition

1) TiO$_2$ dispersion was prepared by dispersing about 50 wt % of TiO$_2$ powder as a diffusion agent in 1,6-hexanediol diacrylate while adjusting 90% particle diameter (D90) in a particle size distribution so as not to exceed 300 nm.

2) QD Ink (Composition 1) was prepared by mixing 80 g of QD dispersion 1, 8 g of TiO$_2$ dispersion, 1 g of TPO-L, and 11 g of 1,6-hexanediol diacrylate.

<Example 2> Preparation of Quantum Dot Composition 1-1. Preparation of Quantum Dots Quantum dots were prepared in the same manner as in Example 1.

1-2. Surface Modification of Quantum Dots

1) Tertiary ligand 3-2 (mono(2-acryloyloxyethyl) succinate, MEAS) according to Formula 3-2 was prepared.

2) The quantum dots were subjected to surface modification twice as in Example 1.

3) The temperature of the solution containing the quantum dots subjected to secondary surface modification was reduced to about 30° C. and 1.19 g of MEAS was added to the solution, which in turn was stirred for about 90 minutes to subject the quantum dots to tertiary surface modification.

4) Reaction was terminated by cooling the solution to room temperature.

1-3. Preparation of Quantum Dot-Monomer Dispersion

QD dispersion 2 was prepared in the same manner as in Example 1.

1-4. Preparation of QD Ink Composition

QD Ink (Composition 2) was prepared in the same manner as in Example 1 except that QD dispersion 2 was used instead of QD dispersion 1.

\<Example 3\> Preparation of Quantum Dot Composition 1-1. Preparation of Quantum Dots
Quantum dots were prepared in the same manner as in Example 1.
1-2. Surface Modification of Quantum Dots
Surface modification was carried out in the same manner as in Example 1 except that Zn-(PEG550-T)$_2$ (secondary ligand 2-2) was used instead of Zn-(BTEGMS)$_2$.
1-3. Preparation of Quantum Dot-Monomer Dispersion
QD dispersion 3 was prepared in the same manner as in Example 1.
1-4. Preparation of QD Ink Composition
QD Ink (Composition 3) was prepared in the same manner as in Example 1 except that QD dispersion 1 with QD dispersion 3 instead of QD dispersion 1.

\<Example 4\> Preparation of Quantum Dot Composition 1-1. Preparation of Quantum Dots
Quantum dots were prepared in the same manner as in Example 1.
1-2. Surface Modification of Quantum Dots
Surface modification was carried out in the same manner as in Example 2 except that Zn-(PEG550-T)$_2$ (secondary Ligand 2-2) was used instead of Zn-(BTEGMS)$_2$.
1-3. Preparation of Quantum Dot-Monomer Dispersion
QD dispersion 4 was prepared in the same manner as in Example 1.
1-4. Preparation of QD Ink Composition
QD Ink (Composition 4) was prepared in the same manner as in Example 1 except that QD dispersion 4 was used instead of QD dispersion 1.

\<Example 5\> Preparation of Quantum Dot Composition 1-1. Preparation of Quantum Dots
Quantum dots were prepared in the same manner as in Example 1.
1-2. Surface Modification of Quantum Dots
Surface modification was carried out in the same manner as in Example 3 except that 1.56 g of a solution of Zn-(PEG550-T)$_2$ (secondary ligand 2-2) diluted to 20 wt % in cyclohexyl acetate was used.
1-3. Preparation of Quantum Dot-Monomer Dispersion
QD dispersion 5 was prepared in the same manner as in Example 1.
1-4. Preparation of QD Ink Composition
QD Ink (Composition 5) was prepared in the same manner as in Example 1 except that QD dispersion 5 was used instead of QD dispersion 1.

\<Example 6\> Preparation of Quantum Dot Composition 1-1. Preparation of Quantum Dots
Quantum dots were prepared in the same manner as in Example 1.
1-2. Surface Modification of Quantum Dots
Surface modification was carried out in the same manner as in Example 4 except that 1.56 g of a solution of Zn-(PEG550-T)$_2$ (secondary ligand 2-2) diluted to 20 wt % in cyclohexyl acetate was used.
1-3. Preparation of Quantum Dot-Monomer Dispersion
QD dispersion 6 was prepared in the same manner as Example 1.
1-4. Preparation of QD Ink Composition
QD Ink (Composition 6) was prepared in the same manner as in Example 1 except that QD dispersion 6 was used instead of QD dispersion 1.

\<Comparative Example 1\> Preparation of Quantum Dot Composition 1-1. Preparation of Quantum Dots
Quantum dots were prepared in the same manner as in Example 1.
1-2. Surface Modification of Quantum Dots
With the temperature of the solution (about 300 g) containing the synthesized quantum dots therein maintained at about 50° C., 6.4 g of a solution of 2-(2-methoxyethoxy) acetic acid (hereinafter referred to as MEAA) diluted to 20 wt % in cyclohexyl acetate was added to the solution, which in turn was stirred for about 5 hours to subject the quantum dots to surface modification. Reaction was terminated by cooling the solution to room temperature
1-3. Preparation of Quantum Dot-Monomer Dispersion
Comparative QD dispersion 1 was prepared in the same manner as Example 1.

\<Comparative Example 2\> Preparation of Quantum Dot Composition 1-1. Preparation of Quantum Dots
Quantum dots were prepared in the same manner as in Example 1.
1-2. Surface Modification of Quantum Dots
The quantum dots were modified in the same manner as in Example 1 except that MTEGT was used instead of MEAA.
1-3. Preparation of Quantum Dot-Monomer Dispersion
Comparative QD dispersion 2 was prepared in the same manner as in Example 1.
1-4. Preparation of QD Ink Composition
QD Ink (Comparative composition 2) was prepared in the same manner as in Example 1 except that Comparative QD dispersion 2 was used instead of QD dispersion 1.

\<Comparative Example 3\> Preparation of Quantum Dot Composition 1-1. Preparation of Quantum Dots
Quantum dots were prepared in the same manner as in Example 1 except that the solution containing the synthesized quantum dots was cooled to room temperature and was subjected to centrifugation with ethanol and acetone to prepare quantum dot powder.
1-2. Surface Modification of Quantum Dots
1) The quantum dot powder was dispersed to about 20 wt % in cyclohexyl acetate.
2) With the temperature of the dispersed quantum dot solution (about 100 g) was maintained at about 60° C., about 15 g of Zn-(BTEGMS)$_2$ (secondary ligand 2-1) was added to the solution, which in turn was stirred for about 3 hours for primary surface modification of the quantum dots.
3) Next, 100 g of a solution of MEAS (tertiary ligand 3-2) diluted to about 20 wt % in cyclohexyl acetate was added to the solution, which in turn was stirred for about 3 hours for secondary surface modification of the quantum dots.

4) Reaction was terminated by cooling the solution to room temperature.

1-3. Preparation of Quantum Dot-Monomer Dispersion

Comparative QD dispersion 3 was prepared in the same manner as in Example 1.

1-4. Preparation of QD Ink Composition

QD Ink (Comparative composition 3) was prepared in the same manner as in Example 1 except that QD Comparative composition 3 was used instead of QD dispersion 1.

<Comparative Example 4> Preparation of Quantum Dot Composition 1-1. Preparation of Quantum Dots Quantum dots were prepared in the same manner as in Example 3.

1-2. Surface Modification of Quantum Dots

The quantum dots were subjected to surface modification in the same manner as in Comparative Example 3 except that about 30 g of Zn-(PEG550-T)$_2$ (secondary ligand 2-2) was used instead of Zn-(BTEGMS)$_2$ (secondary ligand 2-1) in primary surface modification.

1-3. Preparation of Quantum Dot-Monomer Dispersion

Comparative QD dispersion 4 was prepared in the same manner as in Example 1.

1-4. Preparation of QD Ink Composition

QD Ink (Comparative composition 4) was prepared in the same manner as in Example 1 except that QD Comparative composition 4 was used instead of QD dispersion 1.

Examples 1 to 6 and Comparative Examples 1 to 4 are summarized in Table 1.

TABLE 1

| Composition | Ligand | Note |
| --- | --- | --- |
| Composition 1 | MTEGT | |
| | Zn-(BTEGMS)$_2$ | |
| Composition 2 | MTEGT | |
| | Zn-(BTEGMS)$_2$ | |
| | MAES | |
| Composition 3 | MTEGT | Zn-(PEG550-T)$_2$ 0.8 g used |
| | Zn-(PEG550-T)$_2$ | |
| Composition 4 | MTEGT | Zn-(PEG550-T)$_2$ 0.8 g used |
| | Zn-(PEG550-T)$_2$ | |
| | MAES | |
| Composition 5 | MTEGT | Zn-(PEG550-T)$_2$ 1.56 g used |
| | Zn-(PEG550-T)$_2$ | |
| Composition 6 | MTEGT | Zn-(PEG550-T)$_2$ 1.56 g used |
| | Zn-(PEG550-T)$_2$ | |
| | MAES | |
| Comparative QD dispersion 1 | MEAA | Indispensable |
| Comparative composition 2 | MTEGT | |
| Comparative composition 3 | Zn-(BTEGMS)$_2$ MAES | Substitution after QD purification |
| Comparative composition 4 | Zn-(PEG550-T)$_2$ MAES | Substitution after QD purification |

<Experimental Example 1> Measurement of Dispersibility, Absolute Quantum Efficiency (QE), Emission Wavelength, and Full Width of Half Maximum of QD Dispersion QD dispersions 1 to 6 and Comparative QD dispersions 1 to 4 prepared in Examples 1 to 6 and Comparative Examples 1 to 4 were examined for QD precipitation to check dispersibility thereof, and absolute quantum efficiency QE (Otsuka, QE-2000), wavelength and FWHM of the QD dispersions were measured. Results are shown in Table 2.

TABLE 2

| QD | Dispersibility | QE | Wavelength | FWHM |
| --- | --- | --- | --- | --- |
| QD dispersion 1 | Clear | 99.8% | 524 nm | 39 nm |
| QD dispersion 2 | Clear | 99.6% | 523 nm | 39 nm |
| QD dispersion 3 | Clear | 99.5% | 523 nm | 39 nm |
| QD dispersion 4 | Clear | 99.4% | 524 nm | 39 nm |
| QD dispersion 5 | Clear | 99.9% | 523 nm | 39 nm |
| QD dispersion 6 | Clear | 99.4% | 523 nm | 40 nm |
| Comparative QD dispersion 1 | Indispensable | — | — | — |
| Comparative QD dispersion 2 | Clear | 99.4% | 523 nm | 39 nm |
| Comparative QD dispersion 3 | Clear | 99.7% | 523 nm | 40 nm |
| Comparative QD dispersion 4 | Clear | 95.6% | 524 nm | 39 nm |

As shown in Table 2, when only one MEAA was used in the solution in which the quantum dots were synthesized (QD Comparative Dispersion 1), it was confirmed that polarity of the monomer did not match that of the ligand after ligand substitution, causing poor dispersion of the QDs and precipitation. The other dispersions had no precipitation (Clear) and exhibited good dispersion.

When comparing Comparative QD dispersions 1 and 2 prepared using only one ligand, only Comparative QD dispersion 2 was dispersible. It was believed that the presence of more repeated ethylene glycol structures in MTEGT (Comparative QD dispersion 2) than in MEAA (Comparative QD dispersion 1) made the surfaces of the quantum dots more hydrophilic through surface modification, thereby improving dispersibility thereof.

It was confirmed that all dispersions prepared using two or more ligands, such as QD dispersions 1 to 6, had a QE value of 99.4% or more indicating better absolute quantum efficiency than that of Comparative QD dispersion 2 prepared using only one primary ligand (MTEGT).

When comparing the case of allowing ligand substitution immediately after synthesis of quantum dots (QD dispersions 1 to 6) with the case of allowing ligand substitution on QDs separated and purified after synthesis (Comparative QD dispersions 3 and 4), it was confirmed that there was no significant difference in QE value therebetween or the QD dispersions exhibited better QE values. Likewise, it was confirmed that the QD dispersions/comparative QD dispersions had similar values with an emission wavelength of about 523 nm to 524 nm and a full width of half maximum of 39 nm to 40 nm.

Therefore, according to the present invention, ligand substitution immediately after synthesis of QDs was allowed without degradation of QD dispersibility and QE, and provided similar wavelengths and full widths of half maximum to ligand substitution carried out on the purified QDs separated from the corresponding solution, thereby providing no significant difference in performance or better performance than ligand substitution on the purified QDs separated from the corresponding solution.

<Experimental Example 2> Viscosity, Light Absorption Rate and QE of Prepared Composition Viscosity of each of the QD Ink compositions/comparative compositions prepared in Examples 1 to 6 and Comparative Examples 2 to 4 was measured using a viscometer (RheoStress MARS-40, HAAKE) under conditions of room temperature (25° C.) and 100 rpm for 2 minutes, and results are shown in Table 3.

Each of the QD Ink compositions/comparative compositions prepared in Examples 1 to 6 and Comparative Examples 2 to 4 was deposited to a thickness of 10 m on a glass substrate by spin coating (spin coater, Opticoat MS-A150, Mikasa Co., Ltd.), followed by irradiation with UV light at a wavelength of 395 nm and at a dose of 4,000 mJ (83° C., 4 see), thereby preparing a cured film. A 2 cm×2 cm monolayer specimen was loaded on an integrating instrument (QE-2100, Otsuka Electronics Co., Ltd.) to measure an initial light absorption rate and QE (Otsuka, QE-2000). Then, QE was measured after post-bake heat treatment at 180° C. for 30 minutes under a nitrogen atmosphere. Results are shown in Table 3.

It is believed that such characteristics are obtained by reducing ligand deintercalation through more stable binding of the metal-bound secondary ligands (Zn-(BTEGMS)$_2$, Zn-(PEG550-T)$_2$) to the surfaces of the QDs due to greater binding force of the metal-bound secondary ligands than the primary ligand (MTEGT) to which no metal is bound.

When comparing Compositions 1, 3 and 5 using two ligands with Compositions 2, 4 and 6 using three ligands, respectively, it was confirmed that Compositions 2, 4, and 6 had lower viscosities and exhibited less difference in QE values before and after heat treatment. It is believed that such characteristics are obtained by preventing aggregation between the ligands or between the ligands and 1,6-hexanediol diacrylate through addition of the tertiary ligand to induce deintercalation of the primary or secondary ligand, which is simply physically attached to the surfaces of the quantum dots instead of binding thereto.

Compositions 3 and 4 using the secondary ligand 2-2 had a higher viscosity of 25 cP or more and greater differences in QD values before and after heat treatment than Compositions 1 and 2. It is believed that such characteristics are obtained due to a somewhat high molecular weight of Zn-(PEG550-T)2 used as the secondary ligand 2-2, which results in a smaller molar equivalent weight of the secondary ligand 2-2 bound to the QD surfaces than Compositions 1 and 2.

To address this problem, although Compositions 5 and 6 had the same ligand composition as Compositions 3 and 4, the amount of the secondary ligand 2-2 added for QD

TABLE 3

| | Viscosity (cP) | Coating thickness (μm) | Light absorbance | QE (after UV curing) | QE (after UV curing and heat treatment) | QE change rate |
|---|---|---|---|---|---|---|
| Composition 1 | 20.8 | 10.3 | 83.8% | 32.3% | 32.3% | 100.3% |
| Composition 2 | 20.7 | 10.2 | 77.8% | 32.1% | 32.2% | 100.4% |
| Composition 3 | 25.5 | 10.2 | 76.4% | 30.0% | 25.9% | 86.2% |
| Composition 4 | 25.5 | 10.2 | 75.6% | 31.2% | 30.6% | 97.9% |
| Composition 5 | 23.7 | 10.1 | 78.4% | 30.8% | 29.0% | 94.1% |
| Composition 6 | 21.9 | 10.0 | 76.3% | 30.6% | 31.6% | 103.3% |
| Comparative QD dispersion 1 | Not preparable | — | — | — | — | — |
| Comparative composition 2 | 20.4 | 10.0 | 81.8% | 31.4% | 26.4% | 84.2% |
| Comparative composition 3 | 23.0 | 10.1 | 80.5% | 31.2% | 32.1% | 102.9% |
| Comparative composition 4 | 24.5 | 9.9 | 77.1% | 30.6% | 31.5% | 103.0% |

Although not shown in Table 3, quantum dot surface modification was not achieved when the quantum dots were subjected to surface modification with Zn-(BTEGMS)$_2$ (secondary ligand 2-1) directly in the solution containing the quantum dots synthesized therein without primary surface modification with MTEGT (primary ligand). Therefore, it is believed that secondary or tertiary surface modification is possible only after primary surface modification with MTEGT.

As shown in Table 3, it was confirmed that Compositions 1 to 6 using two or more ligands had less difference in QE values before and after heat treatment than Comparative composition 2 using only one ligand, thereby securing good stability (reliability) to external heat and good QD performance in the subsequent heat treatment process required for production of products using a QD composition.

modification in Compositions 5 and 6 was two times that of Compositions 3 and 4. It was confirmed that Compositions 5 and 6 had lower viscosities and better light absorption rates than Compositions 3 and 4, respectively, and achieved great improvement in maintenance of QE values before and after heat treatment. Furthermore, Composition 6 subjected to tertiary modification with the tertiary ligand exhibited better viscosity and optical properties than Composition 5. Therefore, the amount of the secondary ligand and requirement for the tertiary ligand may be adjusted in consideration of desired viscosity, reliability of QE values, and the like by a person having ordinary knowledge in the art.

It was confirmed that, in terms of viscosity, light absorption rate, and QE values (UV-curing, curing, and heat treatment), Compositions 1, 2, 5, and 6 prepared through ligand substitution directly in the solution after QD synthesis had comparable or better properties than Comparative compositions 3 and 4 prepared using the purified QDs separated from the corresponding solution. Accordingly, it was confirmed that the composition according to the present invention allowed ligand substitution directly in the corresponding solution after QD synthesis and could further reduce the viscosity thereof without degradation in light absorption rate and QE.

It should be understood that the present invention is limited to the above example embodiments and various modifications, changes, alterations, and equivalent embodiments can be made by those skilled in the art without departing from the spirit and scope of the present invention.

The invention claimed is:

1. A method for preparing a solventless quantum dot composition, comprising:
   (a) synthesizing quantum dots;
   (b) subjecting the quantum dots to primary surface modification with a primary ligand comprising an ethylene glycol structure without separating the quantum dots from a solution containing the quantum dots synthesized therein;
   (c) subjecting the primary surface-modified quantum dots to secondary surface modification with a secondary ligand represented by Formula 1:

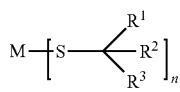

[Formula 1]

(In Formula 1,
M is a bivalent to tetravalent metal,
$R^1$ to $R^3$ are independently hydrogen or a $C_3$ to $C_{70}$ organic group, and
n is an integer of 2 to 4)
   (d) obtaining surface-modified quantum dots from a product of step (c); and
   (e) dispersing the obtained surface-modified quantum dots in a photopolymerizable monomer,
   further comprising: after step (c),
   (f) subjecting the surface-modified quantum dots to tertiary surface modification by adding a $C_3$ to $C_{40}$ tertiary ligand containing a carboxyl group to the solution,
wherein the tertiary ligand is represented by Formula 2

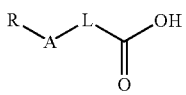

[Formula 2]

(In Formula 2,
L is a single bond or selected from the group consisting of substituted or unsubstituted $C_1$ to $C_{20}$ alkylene groups and substituted or unsubstituted $C_1$ to $C_{20}$ alkenylene groups,
A is a single bond or a $C_1$ to $C_{20}$ alkylene or alkenylene group containing at least one functional group selected from the group consisting of ester (—C(=O)O—), ether (—O—), carbonyl (—C(=O)—), sulfonyl (—SO$_2$—), sulfide (—S—), and sulfoxide (—SO—) groups, and R is hydrogen or selected from the group consisting of substituted or unsubstituted $C_1$ to $C_{20}$ alkyl groups and substituted or unsubstituted $C_1$ to $C_{20}$ alkenyl groups).

2. The method for preparing a solventless quantum dot composition according to claim 1, wherein the primary ligand has a molecular weight of 100 g/mol to 500 g/mol and comprises 1 to 5 repeat units of the ethylene glycol structure, and
wherein at least one of $R^1$ to $R^3$ in Formula 1 comprises repeat units of the ethylene glycol structure,
the total number of repeat units of the ethylene glycol structure contained in $R^1$ to $R^3$ ranges from 2 to 15, and
a $C_1$ to $C_{15}$ organic group is bound to a terminal of the ethylene glycol structure.

3. The method for preparing a solventless quantum dot composition according to claim 1, wherein the quantum dots and the total ligands are mixed in a weight ratio of 1:1 to 1:20.

4. The method for preparing a solventless quantum dot composition according to claim 1, wherein the primary ligand and the secondary ligand added to the solution are present in a mole ratio of 1:1 to 1:20, and
wherein the primary ligand, the secondary ligand and the tertiary ligand added to the solution are present in a mole ratio of 1:1-20:1-30.

5. The method for preparing a solventless quantum dot composition according to claim 1, wherein the primary ligand is at least one selected from the group consisting of methoxy triethylene glycol thioglycolate and 2-(2-methoxyethoxy) acetic acid, and
wherein the secondary ligand is at least one selected from the group consisting of Zn-(3-methoxybutyl 3-mercaptopropionate)$_2$, Zn-(3-methoxybutyl thioglycolate)$_2$, Zn-(2-ethylhexyl thioglycolate)$_2$, Zn-(butyl mercaptopropionate)$_2$, Zn-(isopropyl mercaptopropionate)$_2$, Zn-(bis-(butoxy triethylene glycol) mercapto succinate)$_2$, and Zn-(poly(ethylene glycol) methyl ether-thioglycolate)$_2$, and
wherein the tertiary ligand is at least one selected from the group consisting of 2-carboxyethyl acrylate, mono-2-(acryloyloxy)ethyl succinate, mono-2-(methacryloyloxy)ethyl succinate, mono-2-(methacryloyloxy)ethyl maleate, mono-2-(methacryloyloxy)ethyl maleate, 2-[2-(2-methoxyethoxy) ethoxy]acetic acid, 2-(2-methoxyethoxy) acetic acid, and 2-(2-methoxyethoxy) acetic acid.

6. The method for preparing a solventless quantum dot composition according to claim 1, wherein the solution comprises at least one selected from the group consisting of fatty acids, fatty acid derivatives, by-products of quantum dot synthesis reaction, dioctyl octadecenamide, trioctylphosphine and oxides thereof, n-octadecene, trioctylamine, metal acetate, metal oleate, tris(trimethylsilyl)phosphine, selenium (Se), sulfur(S), selenium-trioctylphosphine, sulfur-trioctylphosphine, chloride salt, and metal chloride.

7. The method for preparing a solventless quantum dot composition according to claim 1, wherein the photopolymerizable monomer is 1,6-hexanediol diacrylate.

8. A solventless quantum dot composition comprising:
quantum dots and a photopolymerizable monomer,
wherein the quantum dots are subjected to surface modification with a primary ligand comprising an ethylene glycol structure and a secondary ligand represented by Formula 1,

[Formula 1]

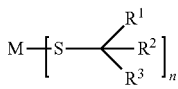

(In Formula 1,

M is a bivalent to tetravalent metal, $R^1$ to $R^3$ are independently hydrogen or a $C_3$ to $C_{70}$ organic group, and n is an integer of 2 to 4)

wherein the surface-modified quantum dots are subjected to surface modification with a $C_3$ to $C_{40}$ tertiary ligand containing a carboxyl group, wherein surface modification of the quantum dots is carried out in a solution containing the quantum dots synthesized therein, wherein the tertiary ligand is represented by Formula 2,

[Formula 2]

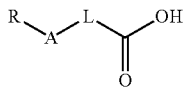

(In Formula 2,

L is a single bond or selected from the group consisting of substituted or unsubstituted $C_1$ to $C_{20}$ alkylene groups and substituted or unsubstituted $C_1$ to $C_{20}$ alkenylene groups, A is a single bond or a $C_1$ to $C_{20}$ alkylene or alkenylene group containing at least one functional group selected from the group consisting of ester (—C(=O)O—), ether (—O—), carbonyl (—C(=O)—), sulfonyl (—SO$_2$—), sulfide (—S—), and sulfoxide (—SO—) groups, and R is hydrogen or selected from the group consisting of substituted or unsubstituted $C_1$ to $C_{20}$ alkyl groups and substituted or unsubstituted $C_1$ to $C_{20}$ alkenyl groups).

9. The solventless quantum dot composition according to claim 8, wherein the primary ligand has a molecular weight of 100 g/mol to 500 g/mol and comprises 1 to 5 repeat units of the ethylene glycol structure.

10. The solventless quantum dot composition according to claim 8, wherein at least one of $R^1$ to $R^3$ in Formula 1 comprises repeat units of the ethylene glycol structure, the total number of repeat units of the ethylene glycol structure contained in $R^1$ to $R^3$ ranges from 2 to 15, and a $C_1$ to $C_{15}$ organic group is bound to a terminal of the ethylene glycol structure.

11. The solventless quantum dot composition according to claim 8, wherein the primary ligand is at least one selected from the group consisting of methoxy triethylene glycol thioglycolate and 2-(2-methoxyethoxy) acetic acid, and wherein the secondary ligand is at least one selected from the group consisting of Zn-(3-methoxybutyl 3-mercaptopropionate)$_2$, Zn-(3-methoxybutyl thioglycolate)$_2$, Zn-(2-ethylhexyl thioglycolate)$_2$, Zn-(butyl mercaptopropionate)$_2$, Zn-(isopropyl mercaptopropionate)$_2$, Zn-(bis-(butoxy triethylene glycol) mercapto succinate)$_2$, and Zn-(poly(ethylene glycol) methyl ether-thioglycolate)$_2$, and wherein the tertiary ligand is at least one selected from the group consisting of 2-carboxyethyl acrylate, mono-2-(acryloyloxy)ethyl succinate, mono-2-(methacryloyloxy)ethyl succinate, mono-2-(methacryloyloxy)ethyl maleate, mono-2-(methacryloyloxy)ethyl maleate, 2-[2-(2-methoxyethoxy) ethoxy]acetic acid, 2-(2-methoxyethoxy) acetic acid, and 2-(2-methoxyethoxy) acetic acid.

12. The solventless quantum dot composition according to claim 8, wherein M is Mg, Ca, Sc, Ti, V, Cr, Mn, Fe, Co, Ni, Cu, Zn, Ga, Ge, Sr, Mo, Pd, Cd, In, or Sn.

13. The solventless quantum dot composition according to claim 8, wherein the primary ligand and the secondary ligand are present in a mole ratio of 1:1 to 1:20, and wherein the primary ligand, the secondary ligand, and the tertiary ligand are present in a mole ratio of 1:1-20:1-30:1 to 20:1 to 30.

14. The solventless quantum dot composition according to claim 8, wherein the quantum dots and the ligands are present in a weight ratio of 1:1 to 1:20.

15. The solventless quantum dot composition according to claim 8, wherein the photopolymerizable monomer is 1,6-hexanediol diacrylate.

16. The solventless quantum dot composition according to claim 8, wherein the solventless quantum dot composition has a viscosity of 30 cP or less.

17. The solventless quantum dot composition according to claim 8, wherein the solventless quantum dot composition is capable of being printed by inkjet.

18. The solventless quantum dot composition according to claim 8, wherein the solventless quantum dot composition is capable of forming a cured film, wherein the cured film has an absolute quantum efficiency of 30% or more at a thickness of 10±0.5 μm.

19. A color filter comprising the solventless quantum dot composition according to claim 8.

20. A display device comprising the color filter according to claim 19.

* * * * *